(12) United States Patent
Wellisz et al.

(10) Patent No.: US 7,048,738 B1
(45) Date of Patent: *May 23, 2006

(54) CRANIAL BONE FLAP FIXATION

(75) Inventors: Tadeusz Z. Wellisz, Los Angeles, CA (US); Cin K. Abidin, Los Angeles, CA (US); Dean Gray, Los Angeles, CA (US)

(73) Assignee: Bioplate, Inc., Los Angeles, CA (US)

( * ) Notice: Subject to any disclaimer, the term of this patent is extended or adjusted under 35 U.S.C. 154(b) by 618 days.

This patent is subject to a terminal disclaimer.

(21) Appl. No.: 10/201,028

(22) Filed: Jul. 23, 2002

(51) Int. Cl.
*A61B 17/58* (2006.01)
(52) U.S. Cl. .......................... 606/70; 606/99
(58) Field of Classification Search ............ 606/69–73, 606/76, 213, 104, 215, 216, 232; 623/17, 623/17.19; 29/243.523; 72/243.528
See application file for complete search history.

(56) References Cited

U.S. PATENT DOCUMENTS

| | | | |
|---|---|---|---|
| 3,540,106 A * | 11/1970 | Goldman ................. | 29/268 |
| 5,250,049 A | 10/1993 | Michael | |
| 5,342,393 A | 8/1994 | Stack | |
| 5,549,620 A | 8/1996 | Bremer | |
| 5,666,710 A * | 9/1997 | Weber et al. .......... | 29/243.523 |
| 5,707,373 A | 1/1998 | Sevrain et al. | |
| 5,800,436 A * | 9/1998 | Lerch ..................... | 606/72 |
| 6,270,500 B1 | 8/2001 | Lerch | |
| 6,379,363 B1 * | 4/2002 | Herrington et al. ........... | 606/79 |
| 6,641,588 B1 * | 11/2003 | Citron et al. ............... | 606/103 |
| 6,755,834 B1 * | 6/2004 | Amis .......................... | 606/72 |
| 2002/0169455 A1 * | 11/2002 | Bannerman et al. ........ | 606/99 |

FOREIGN PATENT DOCUMENTS

| | | |
|---|---|---|
| JP | 5-220174 | 8/1993 |
| SU | 1600713 A1 | 10/1990 |
| WO | WO 00/49949 | 8/2000 |
| WO | WO 02/09602 A1 | 2/2002 |

* cited by examiner

*Primary Examiner*—Anhtuan T. Nguyen
(74) *Attorney, Agent, or Firm*—William W. Haefliger (57) ABSTRACT

A cranial bone and bone flap fixation device, comprising first and second caps between which portions of the cranial bone and bone flap are to be gripped; a longitudinally extending mounting post located to allow relative cap movement lengthwise of an axis defined by the post at least the first cap having protruding structure to extend into a gap formed between the cranial bone and the bone flap to laterally orient the first cap so that peripheral portions thereof will extend over both the cranial bone and the bone flap during fixation.

7 Claims, 7 Drawing Sheets

CRANIAL BONE FLAP FIXATION

BACKGROUND OF THE INVENTION

This invention relates generally to cranial surgery apparatus and method, and more particularly to implant systems and methods for re-fixation of cranial bone flaps after craniotomy.

Cranial bone flaps after craniotomy are typically fixed in position with wire, suture material or mini plates and screws. In some cases, fixation with wire or suture material is not secure. Shifting of the bone flap may result in dislocation, causing depression or protrusion of the flap relative to the adjacent cranium. This phenomenon occurs more frequently with the progressive shift to smaller craniotomies for minimally invasive surgical procedures.

Fixation of the bone flap using mini plates and screws has improved the attachment of the bone flap. This technique, however, demands a considerable amount of time and added cost. There is need for an improved system for fixation of the bone flap to the cranium, providing for quick and easy application, optimal stability, and self guiding or centering of fixation structure relative to the flap bone to the cranium.

SUMMARY OF THE INVENTION

It is a major object of the invention to provide improved flap fixation apparatus, system and methods meeting the above needs. Basically, the fixation device of the invention comprises:

a) first and second caps between which portions of the cranial bone and bone flap are to be gripped, b) a mounting post located to allow relative cap movement lengthwise of an axis defined by the post, c) at least the first cap having protruding structure to extend into a gap formed between the cranial bone and the bone flap to laterally orient the first cap so that peripheral portions thereof will extend over both the cranial bone and the bone flap during fixation, for optimum retention.

An additional object is to provide for cap self centering functionality, by provision of a cap guide configured to extend into a gap formed between the cranial bone and bone flap, to laterally orient the first cap so that portions thereof will overlap the cranial bone and bone flap to approximately equal lateral extents. That guide may have an axially tapering surface or surfaces to project into the gap between edges of said cranial bone and bone flap; and the guide may comprise a cup-shape or tapering tabs, as will be seen. Both caps may incorporate such self-centering functionality.

These and other objects and advantages of the invention, as well as the details of an illustrative embodiment, will be more fully understood from the following specification and drawings, in which:

DETAILED DESCRIPTION

FIGS. 1–4 show a form of the invention, which is preferred. An upper cap 110 in the form of a disc has an outer portion 110*a* extending about the axis of post 113. One arcuate segment 110*a'* of portion 110*a* is intended to engage top surface 119*a* of a cranial bone flap 119; and a second arcuate segment 110*a"* of portion 110*a* is intended to engage top surface 118*a* of cranial bone 118. See FIG. 4. Similarly, a lower cap 130 has an outer portion 130*a* extending about the post, with arcuate segments 130*a'* and 130*a* that engage bottom surfaces 119*c* and 118*c* of 119 and 118. See FIG. 6.

During installation, the upper cap is relatively displaced toward the lower cap, and the caps are tightened against upper and lower surfaces of the cranial bone 118 and bone flap 119. Typically, the lower cap is pulled upwardly toward and against undersides of the flap and cranial bone, during upper cap lowering. Afterwards, the post is severed, adjacent the top surfaces of the upper cap, as seen at 13*d* in FIG. 8.

The post 113 may be serrated as shown at 113*e* to enable one-way ratcheting relative movement of cap 110 toward cap 130, and also to enable positive locking of cap 110 to the post (i.e. serration shoulder angularity to block cap 110 retraction) after desired forcible engagement of both caps with the bone and bone flap 119 and 118. After such locking, the post is severed at region 13*d* close to the cap 110. Positive locking of the cap 110 to the post assures positive retention of the caps in engagement with upper and lower sides of the cranial bone 119 and bone flap 118, and resultant positive positioning of the flap in position relative to cranial bone, during and after replacement of the flap to the skull, promoting healing.

Figure 6:
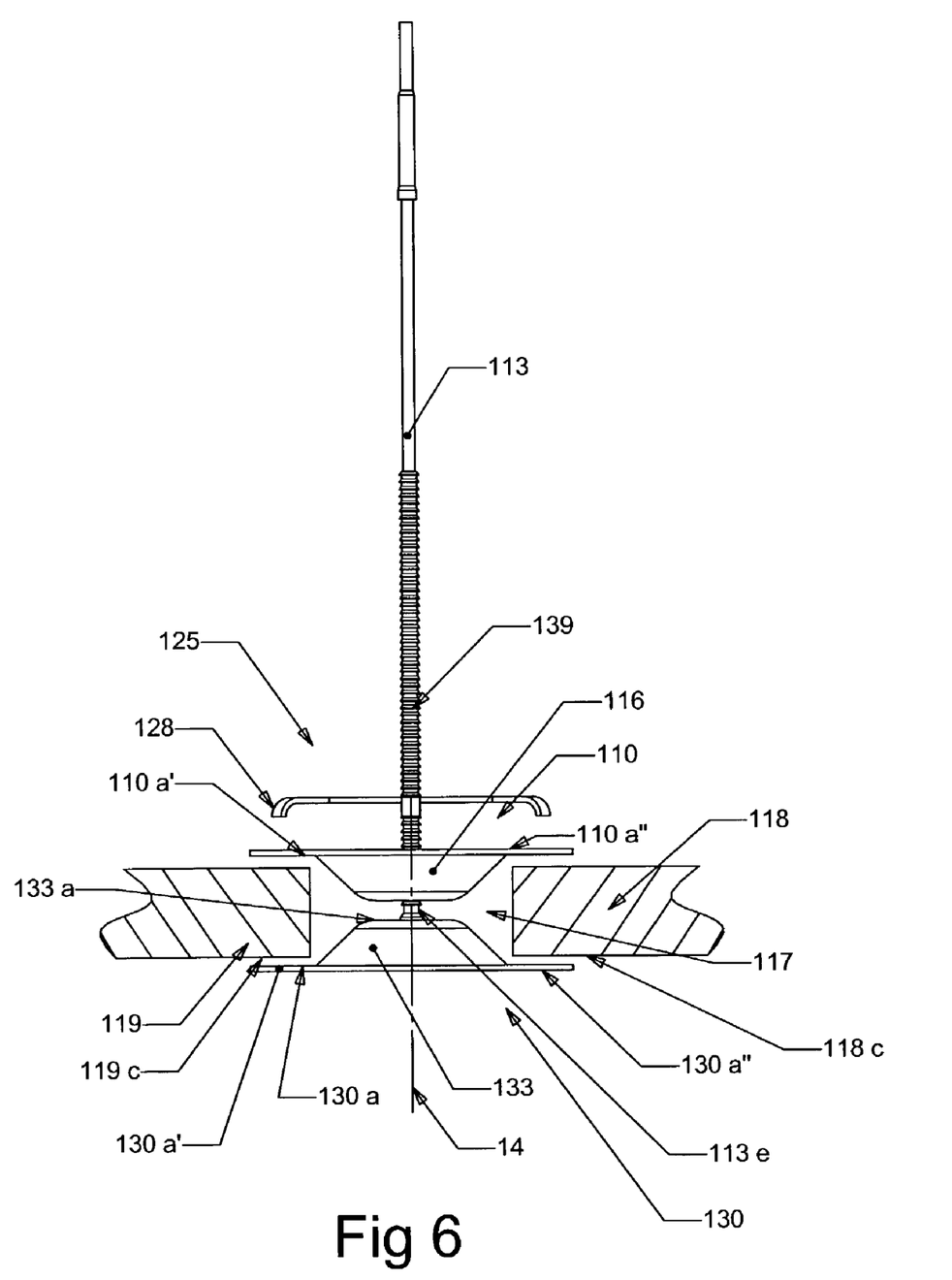
FIG. 6 is an elevation taken in section through the device of FIG. 5 during application to cranial bone and flap elements.
Figure 8:
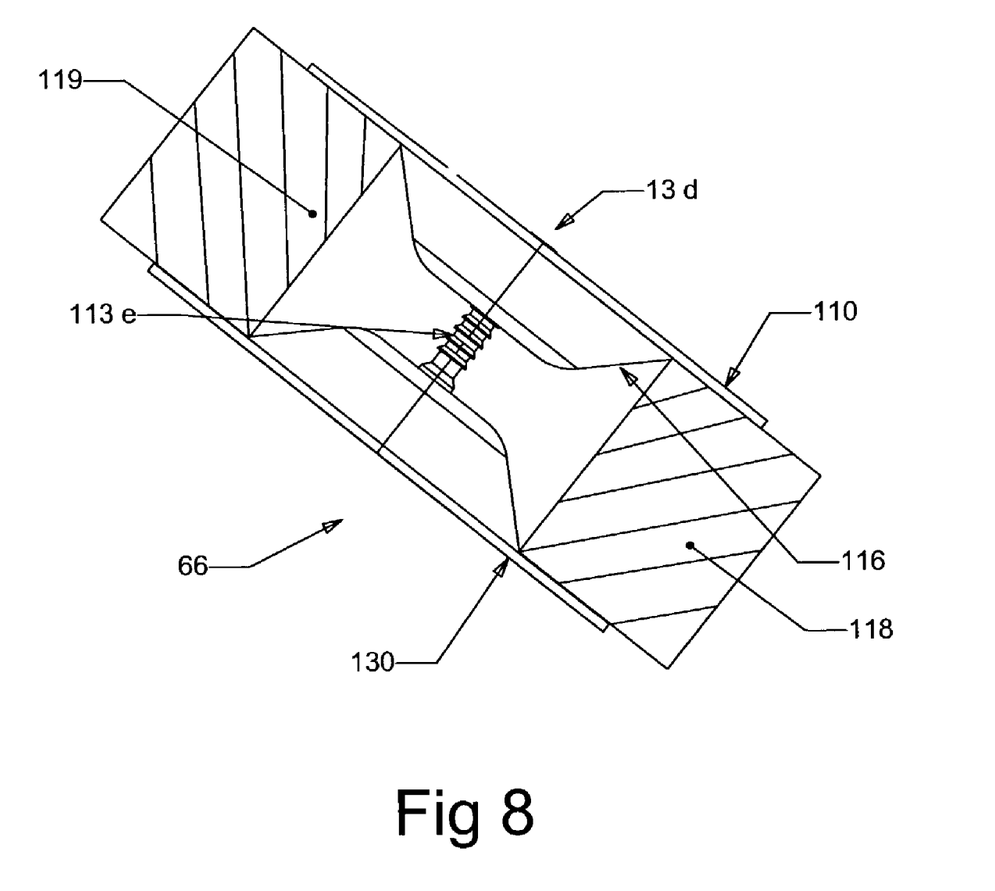
FIG. 8 is an enlarged section showing clamp-up of the upper and lower caps to flap and cranial bone structure.

A protruding guide 116 is formed on, or carried on, the upper cap 110 and configured to extend or project into a gap or kerf 117 formed between cranial bone 118 and bone flap 119, at the time of installation. See FIGS. 4 and 6. The cap is thereby laterally oriented (by engagement of 116 with edges 118*b* and 119*b*) so that the cap portions 110*a'* and 110*a"* of widths indicated at A and B in FIG. 4 will be caused to automatically lap, to approximately equal lateral extents, the adjacent or subtended cranial bone and flap surfaces 118*a* and 119*a*, as a result of clamping installation as seen in FIGS. 6 and 8. Note that the guide under surface 116*a* is generally cup-shaped, or frusto-conical, to project into the gap or kerf 117 between edges 118*b* and 119*b* of the bone surfaces at the gap upper mouth. Three post-engaging and ratcheting tabs 120, are carried by the bottom wall 121*a* of the cup-shaped guide, and a void or cavity exists at 122 above the level of those tabs. Typically, between three and five tabs 120 may be used.

Figure 1:
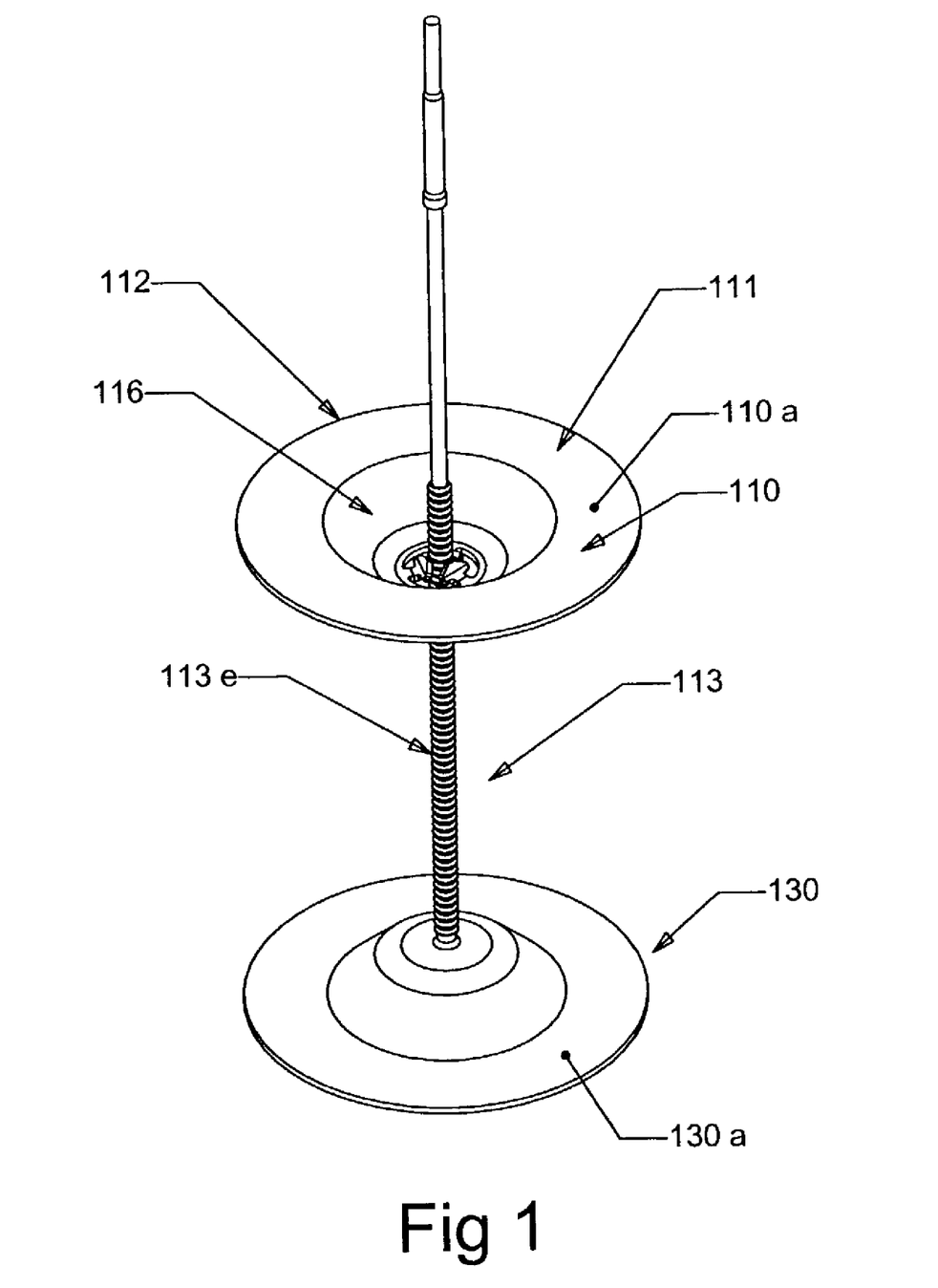
FIG. 1 is a perspective view of a cap, post and guide system incorporating the invention.
Figure 2:
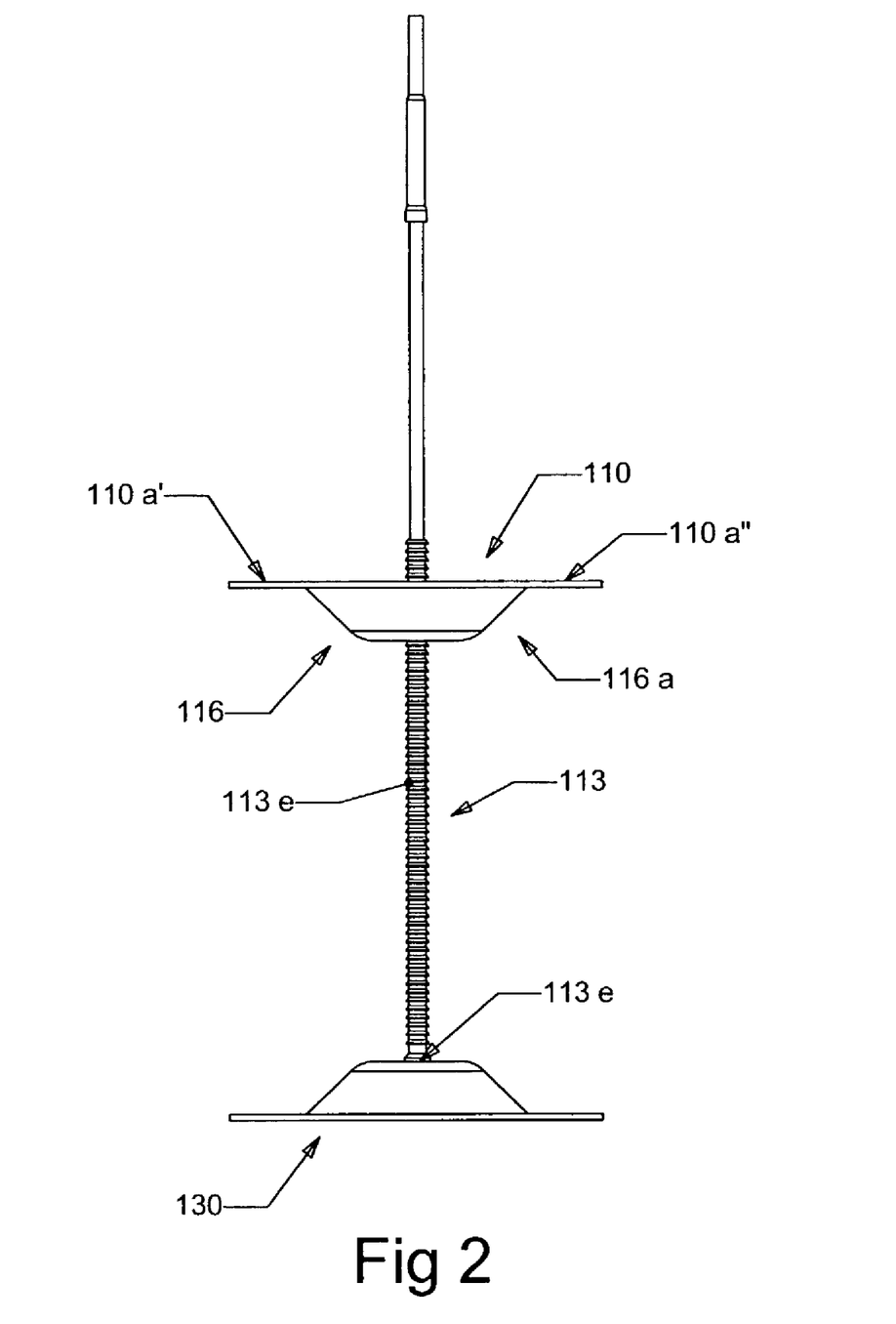
FIG. 2 is an elevational view of the FIG. 1 system.
Figure 3:
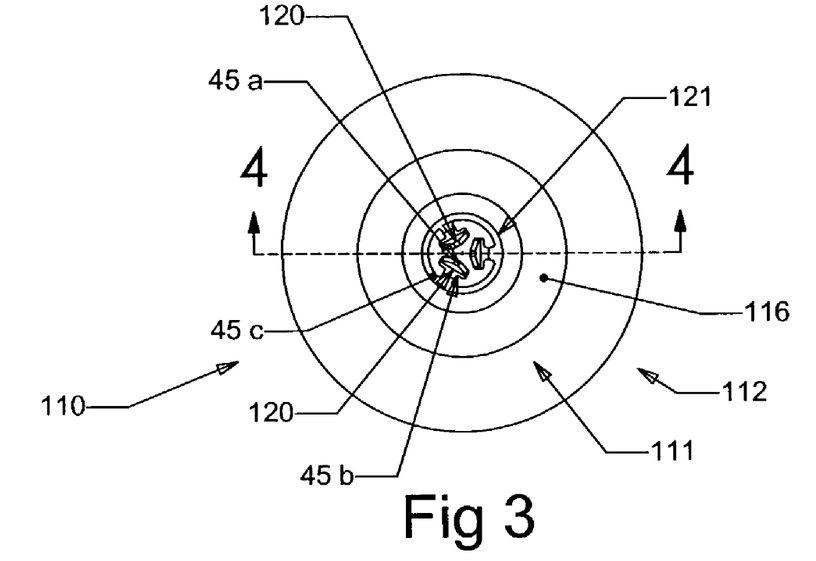
FIG. 3 is a top plan view of the upper cap as also seen in FIGS. 1 and 2.
Figure 4:
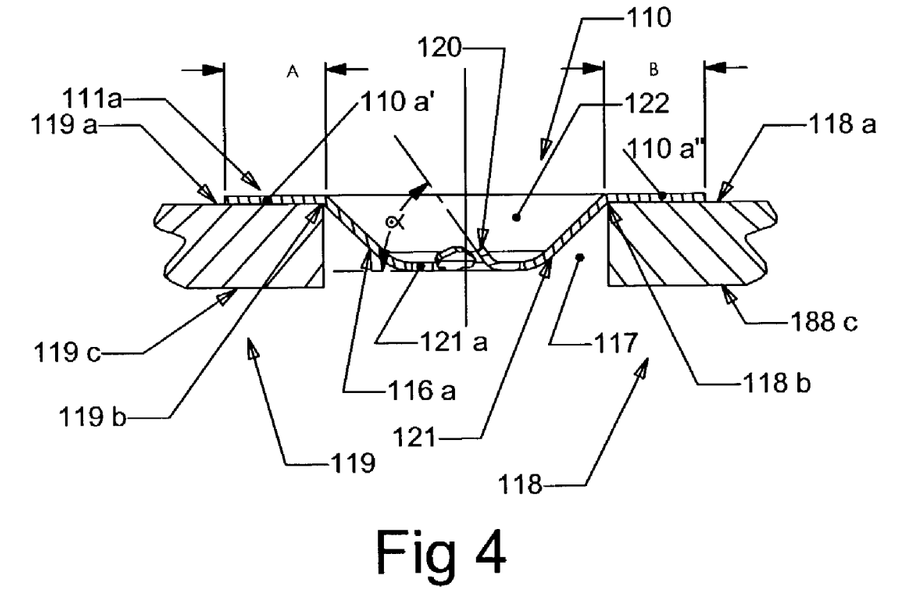
FIG. 4 is a section taken on lines 4—4 of FIG. 3.

The tabs provide one-way ratcheting engagement of tab narrowed inner edges 45*a* seen in FIG. 3 with the post serrations as the upper cap 110 is displaced along the post relatively toward lower cap 130 during installation. The tabs are individually resiliently flexible in directions generally parallel to axis 14, and for that purpose they have narrowed width flexure zones 45*b* located between edges 45*a* and the regions 45*c* of tab jointure with the cup-shaped wall 121*a* of the cap. The tab flexure zones 45*b* have widths less than the tab length, and the tabs extend at angles α out of the transverse plane of lower dished region 121*a* of the guide 116 to further such ratcheting engagement with post serrations, and to facilitate locking of the three tab edges 45*a* into the valley or valleys between successive serrations on the post, to hold the cap regions 110*a*' and 110*a*" compressively against the upper surfaces of the cranial bone and bone flap.

Figure 5:
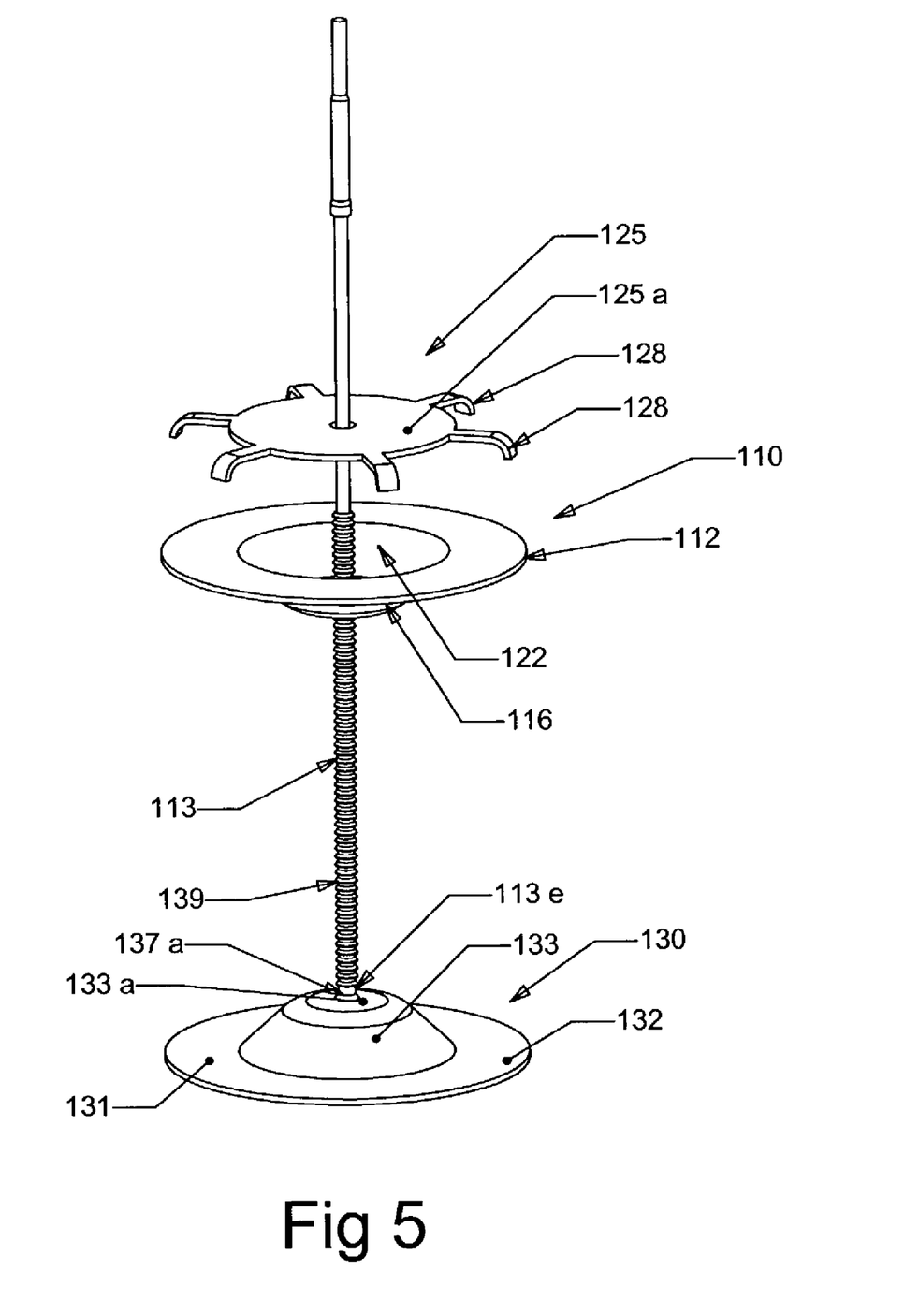
FIG. 5 is a perspective view of a modified form of the system or device.

FIGS. 5 and 6 show the provision of a cover 125 extending over cavity 122 and attached to the cap. Such attachment may be effected by finger-like clips 128 projecting downwardly from the periphery 125*a* of the cover plate to clip onto the outer edge 112 or edge extents of cap 110 outer region 101*a*, plate 125*a* then seating on the upper surface of the disc-like upper cap outer portion 110*a*. Other means of attachment of 125 to 110 may be provided. Such a cover promotes healing of scalp skin over the cap and cover, at generally the same level. The cover is typically applied after the caps are in place, gripping the bone surfaces.

The bottom cap 130 may also have an upwardly protruding inverted cup-shaped guide 133, like guide 116, and is carried by lower cap 130 to function (with self centering) in the same manner as guide 116. See FIG. 6. The lower end 113*e* of post 113 is centrally attached to the end wall 133*a* of the guide 133, and it projects upwardly through 116, whereby tabs 120 can ratchet along post serrations 139, as the two caps relatively approach one another. The two like guides 116 and 133 co-act to enter the discs 110 and 130 relative to the gap or kerf 117.

Figure 7:
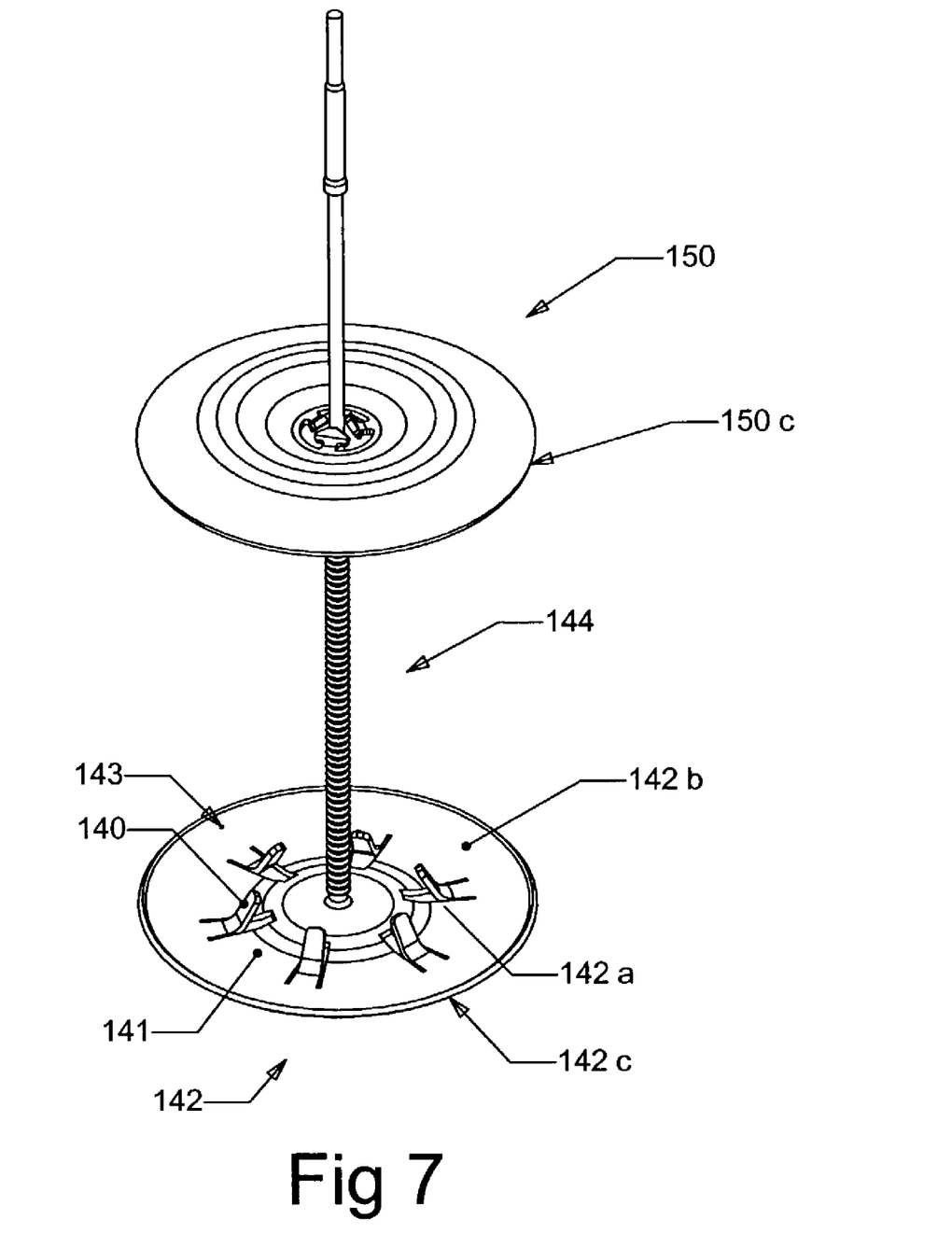
FIG. 7 is a perspective view of yet another modified form of the system or device.

FIG. 7 shows another embodiment of the cap orienting guide, in the form of tabs 140 projecting axially upwardly and inwardly toward the post 144 from the disc-like extent 142*a* of a lower cap 142 also having a disc-like outer annular portion 142*b*. The tabs provide annularly spaced and tapered surfaces engagable with the bone flap and cranial bone lower edges adjacent kerf surfaces or edges referred to in FIGS. 4 and 6, to laterally orient the lower cap, upon assembly. The upper cap 150 may have similar and downwardly projecting tabs to centrally orient it relative to the kerf or gap, upon assembly, for accurately positioning and retaining the flap, relative to the cranial bone. The two caps have outer circular edges 142*c* and 150*c*, so that they are disc-like.

The caps as used may consist of non corrosive metal or metal oxide, an example being titanium dioxide.

We claim:

1. The method of affixing a bone flap to an adjacent cranial zone, that includes
   a) providing upper and lower caps between which portions of the cranial bone and bone flap are to be gripped,
   b) providing a mounting post located to allow relative cap movement lengthwise of an axis defined by the post,
   c) providing protruding structure on at least the upper cap to extend into a gap formed between the cranial bone and the bone flap to laterally orient the upper cap so that peripheral portions thereof will extend over both the cranial bone and the bone flap during fixation,
   d) relatively displacing the caps toward one another so that said protruding structure orients the caps as aforesaid, and to engage one of said caps with at least the bone flap or the adjacent cranial bone, and to conformingly retain the caps to opposite sides of the flap and the cranial zone, and
   e) tightening the caps toward one another into a position wherein relative separation of the caps is blocked, and post extent between the caps is tensioned,
   f) said protruding structure having a thin frusto-conical side wall tapering toward and adapted to penetrate gaps of different widths between said bone flap and proximate cranial bone, said thin tapering side wall locally engaging edges of said bone flap and of said cranial bone, and there being a thin annular lower wall of the protruding structure integral with said tapering side wall and projecting toward the post to form a central opening for passing the post, and there also being at least three tabs confined at and proximate said central opening, said tabs having narrowed flexure zones integral with said lower wall and heads spaced about the post and extending proximate the post and angled toward an interior void bounded by said tapering side wall, for interfering engagement with serrations on the post, as the cap is tightened axially along the post, said tabs everywhere confined below the upper half of said void.

2. The method of affixing a bone flap to an adjacent cranial zone, that includes
   a) providing upper and lower caps between which portions of the cranial bone and bone flap are to be gripped,
   b) providing a mounting post located to allow relative cap movement lengthwise of an axis defined by the post,
   c) relatively displacing the caps toward one another to first engage the lower cap with the underside of at least the bone flap or the adjacent cranial bone,
   d) and then tightening the caps relatively toward one another into positions wherein relative separation of the caps is blocked, the lower cap being pulled upwardly as the upper cap is tightened downwardly,
   e) and providing at least one protruding guide on at least one of said upper and lower caps and configured to extend into a gap formed between the cranial bone and bone flap, to laterally orient the one cap to have approximately equal lateral extents thereof adjacent cranial bone and bone flap surfaces,
   f) said protruding guide having a thin frusto-conical side wall tapering toward and adapted to penetrate gaps of different widths between said bone flap and proximate cranial bone, said thin tapering side wall locally engaging edges of said bone flap and of said cranial bone, and there being a thin annular lower wall of the protruding guide integral with said tapering side wall and projecting toward the post to form a central opening for passing the post, and there also being at least three tabs confined at and proximate said central opening, said tabs having narrowed flexure zones integral with said lower wall and heads spaced about the post and extending proximate the post and angled toward an interior void bounded by said tapering side wall, for interfering engagement with serrations on the post, as the cap is tightened axially along the post, said tabs everywhere confined below the upper half of said void.

3. The method of claim 2 wherein said caps are provided with thin, disc-like outer portions to engage surfaces of the flap and cranial bone.

4. The method of claim 2 wherein said guide has the following:
   i) a conical outer surface on said frusto-conical wall,
   ii) an annular flange projecting from said frusto-conical wall, remotely from said thin lower wall and tabs,
   iii) said tab heads angled toward a plane defined by said annular flange.

5. The method of affixing a bone flap to an adjacent cranial zone, that includes
   a) providing upper and lower caps between which portions of the cranial bone and bone flap are to be gripped,
   b) providing a mounting post located to allow relative cap movement lengthwise of an axis defined by the post,
   c) providing protruding structure on at least the upper cap to extend into a gap formed between the cranial bone and the bone flap to laterally orient the upper cap so that peripheral portions thereof will extend over both the cranial bone and the bone flap during fixation, d) relatively displacing the caps toward one another so that said protruding structure orients the caps as aforesaid, and to engage an angled surface or surfaces defined by the protruding structure with an edge or edges of the bone flap or the adjacent cranial bone, and to conformingly retain the caps to opposite sides of the flap and the cranial zone, and e) tightening the caps toward one another into a position wherein relative separation of the caps is blocked, and post extent between the caps is tensioned, f) said protruding structure having a thin frusto-conical side wall tapering toward and adapted to penetrate gaps of different widths between said bone flap and proximate cranial bone, said thin tapering side wall locally engaging edges of said bone flap and of said cranial bone, and there being a thin annular lower wall of the protruding structure integral with said tapering side wall and projecting toward the post to form a central opening for passing the post, and there also being at least three tabs confined at and proximate said central opening, said tabs having narrowed flexure zones integral with said lower wall and heads spaced about the post and extending proximate the post and angled toward an interior void bounded by said tapering side wall, for interfering engagement with serrations on the post, as the cap is tightened axially along the post, said tabs everywhere confined below the upper half of said void.

6. The method of affixing a cranial bone to a bone flap comprising a) providing first and second caps between which portions of the cranial bone and bone flap are to be gripped, b) providing a mounting post having a cylindrical cross-section and located to allow relative cap movement lengthwise of an axis defined by the post, c) at least the first cap formed to have segments that are spaced apart about said axis and radially outwardly of a central body portion of the cap, whereby the segments are individually and resiliently movable relative to said central body portion in directions generally parallel to said axis, and in response to said gripping, said first cap being movable lengthwise of the post, d) the second cap being attached to an end of the post, and the first cap being adjustably movable along said post toward said second cap, segments of the first cap having peripheral portions spaced from the second cap, e) the post having axially spaced retention shoulders, the first cap having axially downwardly protruding structure forming a central void, the first cap having at least three tabs spaced about and projecting toward said axis, the tabs having terminals projecting into a lower portion of the void, the terminals having ratcheting engagement with said shoulders as said first cap is moved toward said second cap, said retention shoulders formed to unidirectionally lock to the tab terminals, the tabs having short widthwise narrowed flexures being individually resiliently flexible in directions generally parallel to said axis, and the flexures located radially outwardly of said terminals.

7. The device of claim 6 wherein said segments are arcuate.

* * * * *